US00PP31270P2

(12) United States Plant Patent
Heimovaara

(10) Patent No.: US PP31,270 P2
(45) Date of Patent: Dec. 24, 2019

(54) ***ALSTROEMERIA* PLANT NAMED 'ZAPRIMU'**

(50) Latin Name: *Alstroemeria hybrida*
Varietal Denomination: Zaprimu

(71) Applicant: Sjoukje Heimovaara, Oegstgeest (NL)

(72) Inventor: Sjoukje Heimovaara, Oegstgeest (NL)

(73) Assignee: Van Zanten Breeding B.V., Rijsenhout (NL)

( * ) Notice: Subject to any disclaimer, the term of this patent is extended or adjusted under 35 U.S.C. 154(b) by 0 days.

(21) Appl. No.: 16/350,640

(22) Filed: Dec. 14, 2018

(51) Int. Cl.
*A01H 5/02* (2018.01)

(52) U.S. Cl.
USPC ..... Plt./309

(58) Field of Classification Search
USPC ..... Plt./309
CPC ..... A01H 5/02
See application file for complete search history.

(56) References Cited

PUBLICATIONS

Pluto Plant VAriety Database Jul. 5, 2019. p. 1.*

* cited by examiner

*Primary Examiner* — Annette H Para
(74) *Attorney, Agent, or Firm* — C. A. Whealy

(57) ABSTRACT

A new and distinct cultivar of *Alstroemeria* plant named 'Zaprimu', characterized by its compact, upright to outwardly spreading and uniformly mounded plant habit; moderately vigorous growth habit; numerous purple and red purple-colored flowers; and excellent container and garden performance.

2 Drawing Sheets

Botanical designation: *Alstroemeria hybrida.*
Cultivar denomination: 'ZAPRIMU'.

BACKGROUND OF THE INVENTION

The present invention relates to a new and distinct cultivar of *Alstroemeria* plant, botanically known as *Alstroemeria hybrida*, commercially used as a potted and garden-type *Alstroemeria*, and hereinafter referred to by the name 'Zaprimu'.

The new *Alstroemeria* plant is a product of a planned breeding program conducted by the Inventor in Rijsenhout, The Netherlands. The objective of the breeding program is to create new potted *Alstroemeria* plants with uniform plant habit, freely flowering habit, attractive leaf and flower coloration and good garden performance.

The new *Alstroemeria* plant originated from a cross-pollination made by the Inventor in Rijsenhout, The Netherlands in May, 2013 of a proprietary *Alstroemeria hybrida* selection identified as code number 11996-1, not patented, as the female, or seed, parent with a proprietary *Alstroemeria hybrida* selection identified as code number 12609-1, not patented, as the male, or pollen, parent. The new *Alstroemeria* plant was discovered and selected by the Inventor as a single flowering plant from within the progeny of the stated cross-pollination in a controlled greenhouse environment in Rijsenhout, The Netherlands in June, 2014.

Asexual reproduction of the new *Alstroemeria* plant by rhizome divisions in a controlled greenhouse environment in Rijsenhout, The Netherlands since September, 2014 has shown that the unique features of this new *Alstroemeria* plant are stable and reproduced true to type in successive generations.

SUMMARY OF THE INVENTION

Plants of the new *Alstroemeria* have not been observed under all possible combinations of environmental conditions and cultural practices. The phenotype may vary somewhat with variations in environmental conditions such as temperature and light intensity without, however, any variance in genotype. The following traits have been repeatedly observed and are determined to be the unique characteristics of 'Zaprimu'. These characteristics in combination distinguish 'Zaprimu' as a new and distinct *Alstroemeria* plant:

1. Compact, upright to outwardly spreading and uniformly mounded plant habit.
2. Moderately vigorous growth habit.
3. Numerous purple and red purple-colored flowers.
4. Excellent container and garden performance.

Plants of the new *Alstroemeria* can be compared to plants of the female parent selection. Plants of the new *Alstroemeria* differ from plants of the female parent selection primarily in flower color as plants of the new *Alstroemeria* have purple and red purple-colored flowers whereas plants of the female parent selection have dark purple-colored flowers.

Plants of the new *Alstroemeria* can be compared to plants of the male parent selection. Plants of the new *Alstroemeria* differ from plants of the male parent selection primarily in flower color as plants of the new *Alstroemeria* have purple and red purple-colored flowers whereas plants of the male parent selection have red purple-colored flowers.

Plants of the new *Alstroemeria* can be compared to plants of *Alstroemeria hybrida* 'Zaprilian', disclosed in U.S. Plant Pat. No. 22,042. In side-by-side comparisons, plants of the new *Alstroemeria* differ primarily from plants of 'Zaprilian' in flower color as plants of the new *Alstroemeria* have purple and red purple-colored flowers whereas plants of 'Zaprilian' have light purple-colored flowers. In addition, plants of the new *Alstroemeria* are broader than plants of 'Zaprilian'.

BRIEF DESCRIPTION OF THE PHOTOGRAPHS

The accompanying colored photographs illustrate the overall appearance of the new *Alstroemeria* plant showing the colors as true as it is reasonably possible to obtain in colored reproductions of this type. Colors in the photographs may differ slightly from the color values cited in the detailed botanical description which accurately describe the colors of the new *Alstroemeria* plant.

The photograph on the first sheet is a top perspective view of a typical flowering plant of 'Zaprimu'.

The photograph on the second sheet is a close-up view of typical leaves and flowers of 'Zaprimu'.

DETAILED BOTANICAL DESCRIPTION

The aforementioned photographs and following observations and measurements describe plants of the new *Alstroemeria* grown during the spring in 14-cm containers in a glass-covered greenhouse in Rijsenhout, The Netherlands. During the production of the plants, day temperatures ranged from 15° C. to 25° C., night temperatures ranged from 10° C. to 15° C., soil temperatures averaged 14° C. and light levels averaged 5,000 lux. Plants were three months old when the photographs and description were taken. In the following description, color references are made to The Royal Horticultural Society Colour Chart, 2015 Edition, except where general terms of ordinary dictionary significance are used.

Botanical classification: *Alstroemeria hybrida* 'Zaprimu'.

Parentage:

- *Female, or seed, parent.*—Proprietary *Alstroemeria hybrida* selection identified as code number 11996-1, not patented.
- *Male, or pollen, parent.*—Proprietary *Alstroemeria hybrida* selection identified as code number 12609-1, not patented.

Propagation:

- *Type.*—In vitro rhizogenesis.
- *Time to produce a rooted young plant, summer.*—About 40 days at temperatures of 16° C. to 25° C.
- *Time to produce a rooted young plant, winter.*—About 60 days at temperatures of 16° C. to 20° C.
- *Root description.*—Fibrous, fleshy, thick; color, close to 155D.
- *Rooting habit.*—Freely branching; medium density.
- *Rhizomes.*—Shape: Elongate; rounded. Length: About 10 cm to 30 cm. Diameter: About 3 mm to 10 mm. Texture: Smooth. Color: Close to 155D.

Plant description:

- *Plant and growth habit.*—Compact, upright to outwardly spreading and uniformly mounding plant habit; freely branching habit with about five to six primary lateral branches each with about three secondary lateral branches, dense and bushy appearance; moderately vigorous growth habit; moderate growth rate.
- *Plant height.*—About 27 cm.
- *Plant diameter* (*spread*).—About 45 cm.

Lateral branch description:

- *Length.*—About 21 cm.
- *Diameter.*—About 2 mm.
- *Internode length.*—About 1 cm.
- *Strength.*—Moderately strong.
- *Aspect.*—About 45° from vertical.
- *Texture and luster.*—Smooth, glabrous; semi-glossy.
- *Color, developing and fully developed.*—Close to 138C.

Leaf description:

- *Arrangement.*—Alternate; simple.
- *Length.*—About 8 cm to 11 cm.
- *Width.*—About 3 cm to 4 cm.
- *Shape.*—Lanceolate.
- *Apex.*—Acute.
- *Base.*—Cuneate.
- *Margin.*—Entire.
- *Texture and luster, upper surface.*—Smooth, glabrous; semi-glossy.
- *Texture and luster, lower surface.*—Ribbed; matte.
- *Aspect.*—Upright to somewhat horizontal, twisting.
- *Venation pattern.*—Parallel.
- *Color.*—Developing leaves, upper and lower surfaces: Close to 137A. Fully expanded leaves, upper surface: Close to 137A; venation, close to N138B. Fully expanded leaves, lower surface: Close to 145A; venation, close to 145B.
- *Petioles.*—Length: About 1.5 cm. Diameter: About 4 mm. Texture and luster: Smooth, glabrous; matte. Strength: Low, flexible. Color, upper surface: Close to 137A. Color, lower surface: Close to N138B.

Flower description:

- *Flower type and habit.*—Single cup-shaped flowers arranged in compound umbels; flowers face upright to outwardly; perianth segments separate; freely flowering habit with about 30 flower buds and flowers per plant at one time.
- *Natural flowering season.*—Flowering continuous from the spring until the autumn in The Netherlands; early flowering habit, plants begin flowering about 70 to 80 days after planting.
- *Fragrance.*—None detected.
- *Flower longevity on the plant.*—About ten days; flowers not persistent.
- *Flower buds.*—Length: About 3 cm. Diameter: About 1.5 cm. Shape: Roughly ovoid. Texture and luster: Smooth, glabrous; semi-glossy. Color: Close to 186C and 155A.
- *Umbel height.*—About 10 cm.
- *Umbel diameter.*—About 10 cm.
- *Flower diameter.*—About 5 cm by 7 cm.
- *Flower depth.*—About 6 cm.
- *Perianth.*—Arrangement: Six arranged in two whorls, each whorl with two lateral and one median segments. Inner perianth, lateral segments: Length: About 6 cm. Width: About 2 cm. Shape: Oblanceolate. Apex: Wishbone-shaped and acuminate. Base: Attenuate. Margin: Proximally, entire and distally, dentate; somewhat undulate. Texture and luster, upper surface: Smooth, glabrous; semi-glossy. Texture and luster, lower surface: Ribbed; matte. Color, when opening and fully opened, upper surface: Proximally, close to 76C; mid-section, close to 155A; distally, close to N75B and 70A; apex, close to 140A; stripes, close to 187A; with development, distal color becoming closer to N77B. Color, when opening and fully opened, lower surface: Proximally, close to 76D; mid-section, close to 70B; distally, close to N75D; color does not change with development. Inner perianth, median segment: Length: About 5.5 cm. Width: About 2 cm. Shape: Oblanceolate. Apex: Wishbone-shaped and acuminate. Base: Attenuate. Margin: Proximally, entire and distally, dentate; somewhat undulate. Texture and luster, upper surface: Smooth, glabrous; semi-glossy. Texture and luster, lower surface: Ribbed; matte. Color, when opening and fully opened, upper surface: Proximally, close to 76C; mid-section, close to 155A; distally, close to N75B and 70A; apex, close to 140A; stripes, close to 187A; with development, distal color becoming closer to 76A and N77B. Color, when opening and fully opened, lower surface: Proximally, close to 76D; mid-section, close to 70B; distally, close to N75D; color does not change with development. Outer perianth, lateral segments: Length: About 6 cm. Width: About 3 cm. Shape: Obovate. Apex: Embedded point. Base: Attenuate. Margin: Entire; somewhat undulate. Texture and luster, upper surface: Ribbed; semi-glossy. Texture and luster, lower surface: Ribbed; matte. Color, when opening and fully opened, upper surface: Close to N75B; center, close to 70A; apex, close to 141C; with development, color becoming closer to 70A and center, closer to N77B. Color, when opening and fully opened, lower surface: Close to N75D and 70B; apex and venation, close to 141C; color does not change with development. Outer perianth, median segment: Length: About 6 cm. Width: About 3.2 cm. Shape: Obovate. Apex: Embedded point. Base: Attenuate. Margin: Entire; somewhat undulate. Texture and luster, upper surface: Ribbed; semi-glossy. Texture and luster, lower surface: Ribbed; matte. Color, when opening and fully opened, upper surface: Close to N75B; center, close to 70A; apex, close to 141C; with development, color becoming closer to 70A and center, closer to N77B. Color, when opening and fully opened, lower surface: Close to N75D and 70B; apex and venation, close to 141C; color does not change with development.

*Pedicels*.—Length: About 2.5 cm. Diameter: About 1.5 mm. Strength: Strong. Angle: About 25° from vertical. Texture and luster: Smooth, glabrous; semi-glossy. Color: Close to 138B.

*Reproductive organs*.—Stamens: Quantity per flower: Typically six. Filament length: About 3.5 cm to 4 cm. Filament color: Close to N75A. Anther size: About 0.8 mm by 2 mm. Anther shape: Elliptical. Anther color: Close to 187A. Pollen amount: Abundant. Pollen color: Close to 187B. Pistils: Quantity per flower: One. Style length: About 3 cm. Style color: Close to N75A. Stigma diameter: About 0.7 mm. Stigma shape: Three-parted. Stigma color: Close to N75A. Ovary color: Close to 138A.

*Fruits and seeds*.—To date, fruit and seed development have not been observed on plants of the new *Alstroemeria*.

Pathogen & pest resistance: To date, plants of the new *Alstroemeria* have not been observed to be resistant to pathogens and pests common to *Alstroemeria* plants.

Garden performance: Plants of the new *Alstroemeria* have been observed to have excellent garden performance and to tolerate wind, rain, temperatures from about −5° C. to about 40° C. and to be suitable for USDA Hardiness Zone 9.

It is claimed:

1. A new and distinct *Alstroemeria* plant named 'Zaprimu' as illustrated and described.

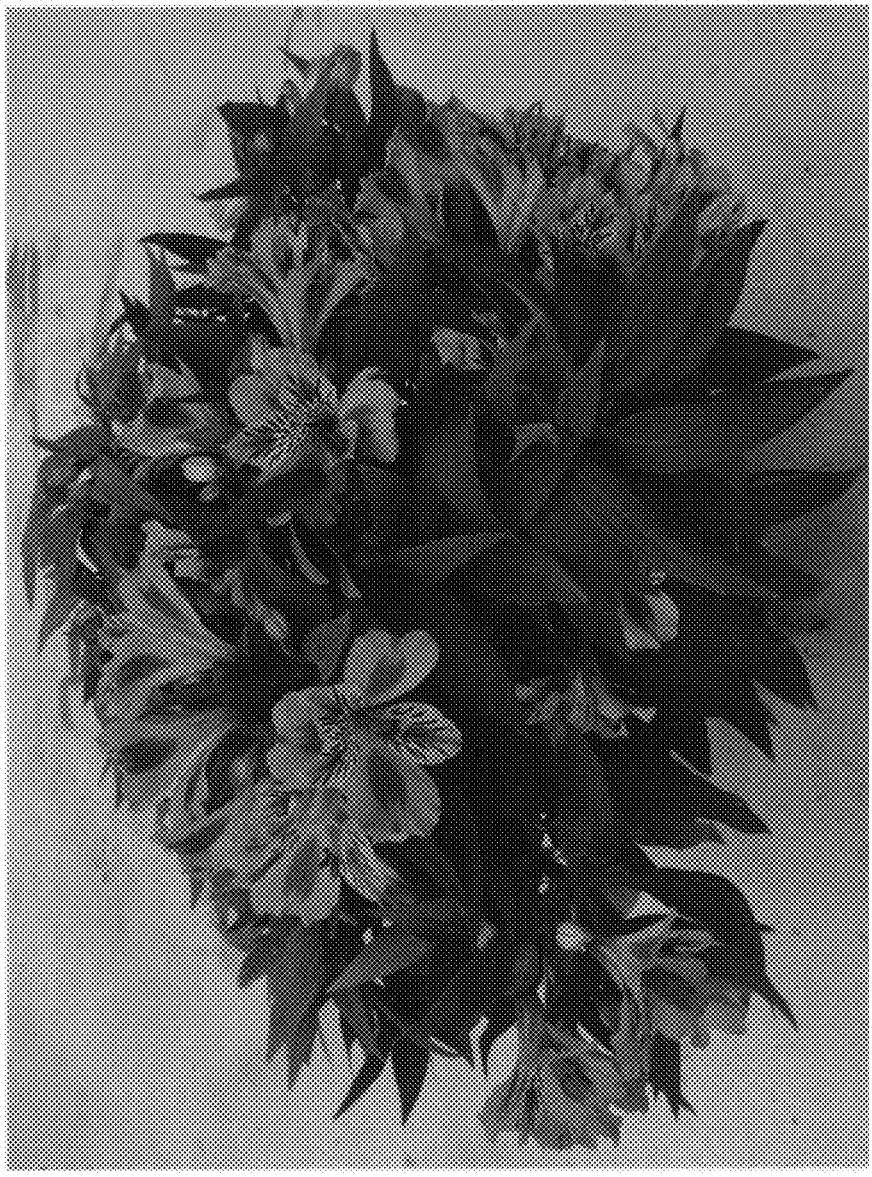

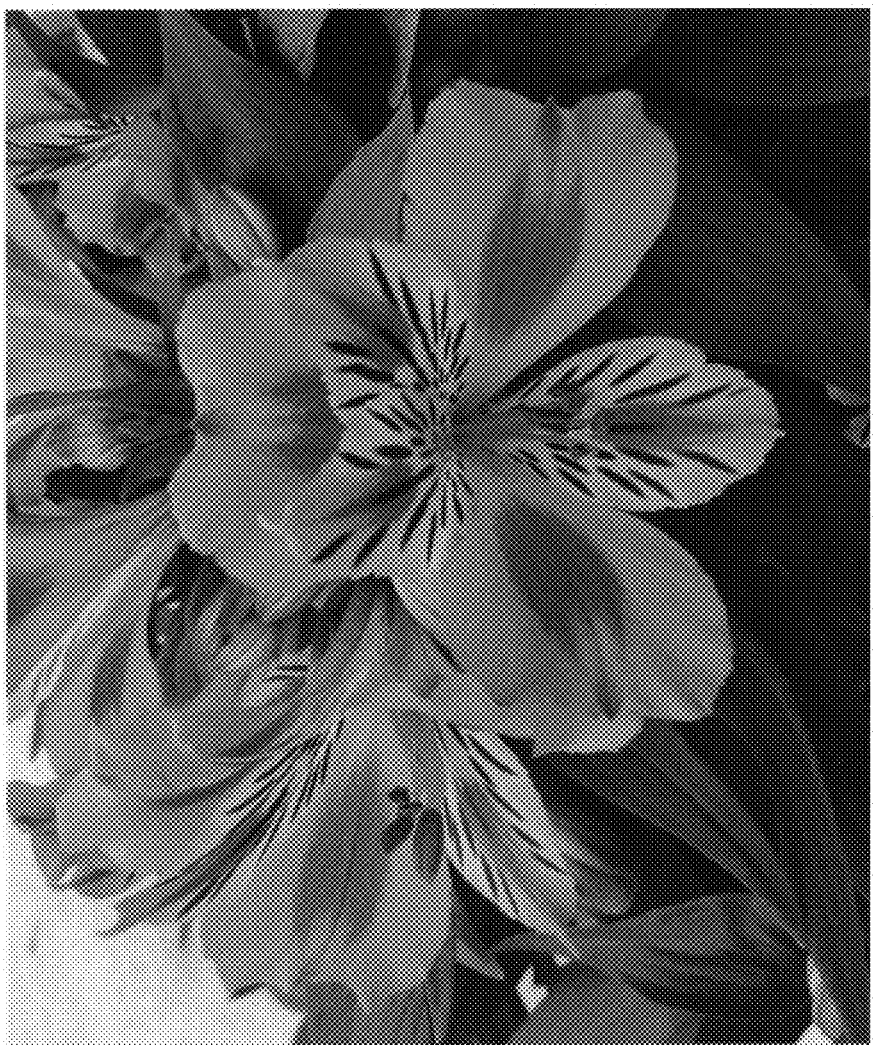

* * * * *